US00PP09592P

United States Patent [19]

Jolly

[11] Patent Number: Plant 9,592

[45] Date of Patent: Jun. 25, 1996

[54] FLORIBUNDA ROSE PLANT NAMED 'JOLLMEA'

[76] Inventor: Marie Jolly, Gregg Neck Rd., Galena, Md. 21635

[21] Appl. No.: 514,621

[22] Filed: Aug. 15, 1995

[51] Int. Cl.[6] ..... A01H 5/00

[52] U.S. Cl. ..... Plt./22

[58] Field of Search ..... Plt./1, 11, 22

*Primary Examiner*—Howard J. Locker

[57] ABSTRACT

A new and distinct variety of rose plant of the floribunda rose class characterized by its abundant blooming habit of growth and unusual color.

1 Drawing Sheet

BACKGROUND OF THE NEW PLANT

The present invention relates to a new and distinct variety of rose plant of the Floribunda rose class named "Jollmea," which was originated by my crossing as seed parent the rose known as "Crimson Glory" (U.S. Plant Pat. No. 105)× "Orange Honey" (U.S. Plant Pat. No. 4,496) as pollen parent.

Among the novel characteristics possessed by this new variety which distinguishes it from all other varieties of which I am aware are:

1. Unusual blending of flower color of a pure ivory white with an overlay of a red deeper than (Red Purple Group 66 A);

2. An exquisite flower form in that each petal recurls in a quilled manner;

3. The plant is low and compact with medium sized glossy foliage;

4. Shows outstanding resistance to disease and is winter hardy

Asexual reproduction by budding of the new variety as performed in West Grove, Pa. and McFarland, Calif., shows that the foregoing and other distinguishing characteristics come true to form and are established and transmitted through succeeding propagation.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "66-A" is plate 66-A of the Royal Society Colour Chart.

DESCRIPTION OF THE NEW VARIETY

Flower

A. Bud:
- (1) *Size.*—Medium.
- (2) *Form.*—Pointed.
- (3) *Color.*—Ivory white with pink markings.
- (4) *Sepals.*—Slightly longer than bud.
- (5) *Peduncle.*—Short and erect with a smooth surface and medium green color nearest to 141-B.

B. Bloom:
- (1) *Size.*—Medium 10–11½ cm.

- (2) *Borne.*—Mostly erect.
- (3) *Form.*—High centered and quilled as opened.
- (4) *Petalage.*—Heavy number of petals under normal conditions. (38).
- (5) *Color.*—Ivory white with a red overlay (near 50A).
- (6) *Color change.*—Blends from 50-A to 66-A as petals open.

C. Petals:
- (1) *Texture.*—Average thickness.
- (2) *Appearance.*—Inside: velvety. Outside: Satiny. Gives veiny appearance as color blends.
- (3) *Form.*—Tips recurled and quilled.
- (4) *Arrangement.*—Imbricated regularly.
- (5) *Petaloids in center.*—Few.
- (6) *Persistence.*—Drop off cleanly.
- (7) *Fragrance.*—Moderate.
- (8) *Lasting quality.*—Good on plant and when cut.

Reproductive Organs

A. Stamens: Regularly arranged around the pistil.
- (1) *Anthers.*—Color near 17-C.
- (2) *Pollen.*—Color near 14-B.

B. Pistils:
- (1) *Styles.*—Greenish white near 150-D.
- (2) *Stigmas.*—Color near 26-C.

C. Hips: Near 34-C.

Plant

A. Form: Bushy and upright.

B. Growth: Uniform branching, compact with good vigor. Height of plant is 105 cm.

C. Blooming habit: Continuous blooming throughout growing season.

D. Foliage: Compounded 3–5 leaflets on single bloom, 5–7 leaflets on main canes.
- (1) *Size.*—Medium.
- (2) *Quantity.*—Abundant covers plant to ground.
- (3) *Color.*—1) Upperside — Near to 136-A with deep green. 2) Underside — Grayish green to 136-C.
- (4) *Shape.*—Oval.
- (5) *Texture.*—a) Upper side — Leathery, glossy. b) Under side — Smooth.
- (6) *Edge.*—Serrated.
- (7) *Serration.*—Small.
- (8) *Leaf stem.*—Color is 137-B, underside is 137-C.
- (9) *Stipules.*—Smooth.

E. Wood:
- (1) *New wood.*—a) Color — 137-C. b) Bark — Smooth.
- (2) *Old wood.*—a) Color — 137-B. b) Bark — Smooth.

F. Thorns:

(1) *Quantity.*—Few.
(2) *Form.*—Flat base.
(3) *Length.*—Medium.
(4) *Color.*—148C.
(5) *Position.*—Regular.

G. Prickles:
(1) *Quantity.*—Few.

H. Plant's disease resistance:

(1) *Mildew.*—Good.
(2) *Blackspot.*—Good.
(3) *Rust.*—Good.

I. Winter hardiness: Good.

I claim:

1. A new and distinct variety of rose plant of the Floribunda class, substantially as shown and described.

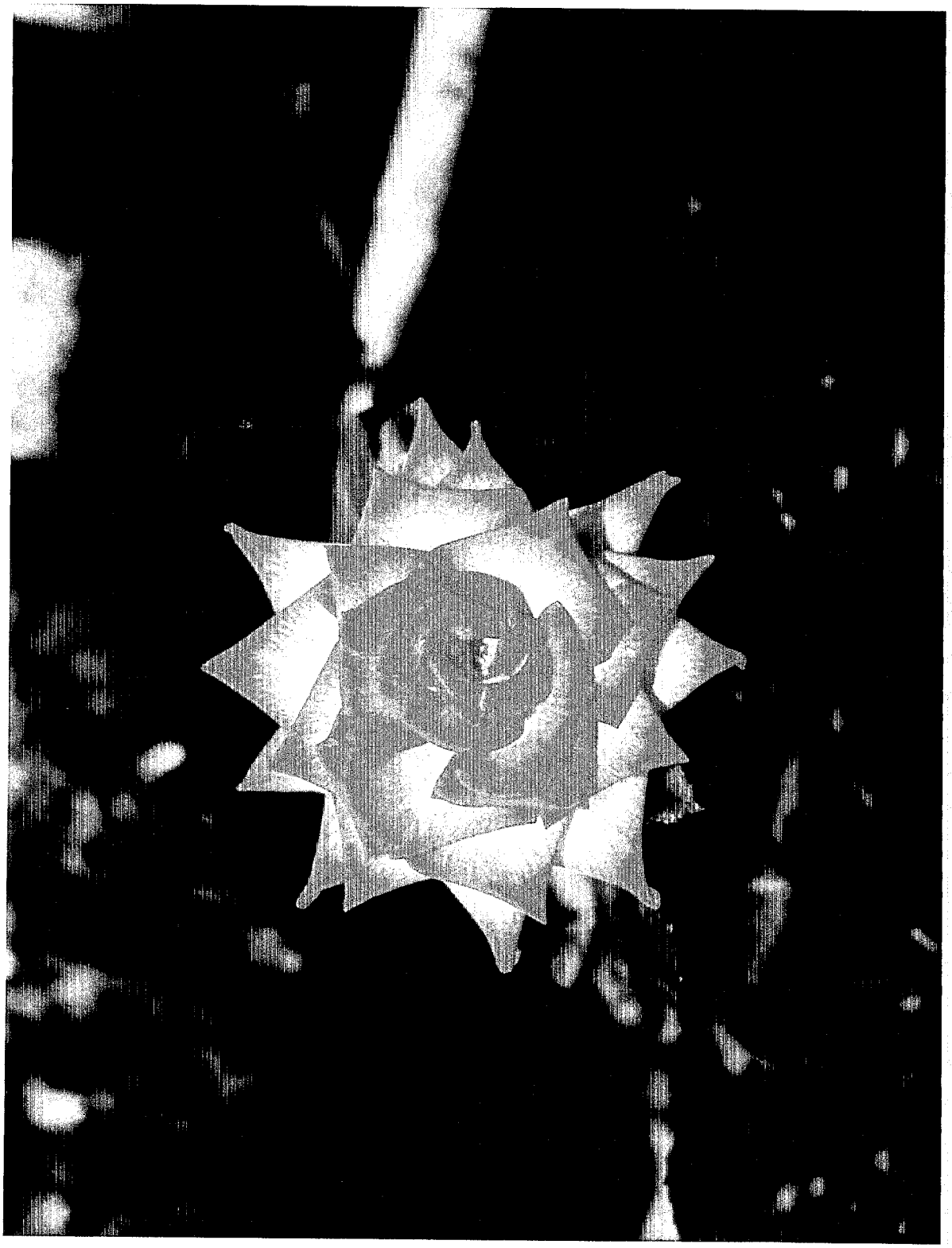

* * * * *